US010786782B2

(12) United States Patent
Fujimori et al.

(10) Patent No.: US 10,786,782 B2
(45) Date of Patent: Sep. 29, 2020

(54) GAS TREATMENT METHOD

(71) Applicant: SEKISUI CHEMICAL CO., LTD., Osaka (JP)

(72) Inventors: Yoji Fujimori, Ibaraki (JP); Tetsuya Ishii, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/759,390

(22) PCT Filed: Sep. 16, 2016

(86) PCT No.: PCT/JP2016/077374
§ 371 (c)(1),
(2) Date: Mar. 12, 2018

(87) PCT Pub. No.: WO2017/047730
PCT Pub. Date: Mar. 23, 2017

(65) Prior Publication Data
US 2018/0257034 A1    Sep. 13, 2018

(30) Foreign Application Priority Data

Sep. 17, 2015 (JP) .................................. 2015-183976

(51) Int. Cl.
*B01D 53/14* (2006.01)
*B01D 53/86* (2006.01)
(Continued)

(52) U.S. Cl.
CPC ......... *B01D 53/8612* (2013.01); *B01D 53/14* (2013.01); *B01D 53/1406* (2013.01);
(Continued)

(58) Field of Classification Search
None
See application file for complete search history.

(56) References Cited

U.S. PATENT DOCUMENTS

| 5,057,291 A | 10/1991 | Fisher et al. |
| 7,060,233 B1 * | 6/2006 | Srinivas ................ B01D 53/64 |
| | | 423/210 |

(Continued)

FOREIGN PATENT DOCUMENTS

| JP | 5-117669 | 5/1993 |
| JP | 7-81901 | 3/1995 |

(Continued)

OTHER PUBLICATIONS

International Search Report dated Oct. 18, 2016 in International (PCT) Application No. PCT/JP2016/077374.

(Continued)

*Primary Examiner* — Sheng H Davis
(74) *Attorney, Agent, or Firm* — Wenderoth, Lind & Ponack, L.L.P.

(57) ABSTRACT

It is an object of the present invention to downsize facility for removing or reducing concentration of hydrogen sulfide and oxygen in gas and reduce facility cost. Syngas g contains hydrogen sulfide and oxygen as target constituents of removal or reduction in concentration. Hydrogen sulfide content and oxygen content in the syngas g are measured in a preceding measurement part 13. Then, the syngas g is contacted with desulfurizing agent 14*a* including iron oxide. Selection is made whether to further execute deoxidization in a deoxidizing part 16 or omit or simplify the deoxidization according to results of measurements in the preceding measurement part 13.

3 Claims, 2 Drawing Sheets

(51) Int. Cl.
    *B01D 53/52*     (2006.01)
    *C12P 1/04*     (2006.01)
    *B01D 53/72*     (2006.01)

(52) U.S. Cl.
    CPC ......... *B01D 53/1487* (2013.01); *B01D 53/52* (2013.01); *B01D 53/72* (2013.01); *C12P 1/04* (2013.01); *B01D 2257/104* (2013.01); *B01D 2257/304* (2013.01)

(56) References Cited

U.S. PATENT DOCUMENTS

| | | | |
|---|---|---|---|
| 2003/0194366 A1* | 10/2003 | Srinivas | B01D 53/8612 423/230 |
| 2005/0100504 A1* | 5/2005 | Geus | C01B 17/0469 423/573.1 |
| 2009/0107333 A1* | 4/2009 | Farha | B01D 15/00 95/138 |
| 2012/0052541 A1 | 3/2012 | Oakley | |
| 2012/0285863 A1* | 11/2012 | McLauchlan | B01D 53/1425 208/178 |
| 2013/0260443 A1* | 10/2013 | Varani | B01D 53/48 435/266 |
| 2014/0271451 A1* | 9/2014 | Buccini | B01D 53/1468 423/658.3 |

FOREIGN PATENT DOCUMENTS

| | | |
|---|---|---|
| JP | 2005-154503 | 6/2005 |
| JP | 2007-830 | 1/2007 |
| JP | 2011-502040 | 1/2011 |
| JP | 2012-149138 | 8/2012 |
| JP | 2014-50406 | 3/2014 |

OTHER PUBLICATIONS

International Preliminary Report on Patentability dated Mar. 20, 2018 in International (PCT) Application No. PCT/JP2016/077374.
Extended European Search Report dated Apr. 25, 2019 in corresponding European patent application No. 16846601.9.
Office Action dated Apr. 3, 2020 in corresponding Chinese Patent Application No. 201680053933.4, with Machine translation.

* cited by examiner

GAS TREATMENT METHOD

FIELD OF THE INVENTION

The present invention relates to a method for treating gas containing hydrogen sulfide and oxygen, and particularly relates to a method for treating gas to remove or reduce in concentration of the hydrogen sulfide and the oxygen in the gas.

BACKGROUND OF THE INVENTION

For example, in Patent Document 1, valuable materials such as ethanol are produced by fermentative action of anaerobic microorganisms using syngas (synthetic gas) containing carbon monoxide and hydrogen. The syngas contains constituents such as hydrogen sulfide and oxygen. These constituents may be harmful to the microorganisms, and therefore, Patent Document 1 mentions removing these constituents in a pretreatment step.

PRIOR ART DOCUMENTS

Patent Documents

Patent Document 1: Japanese Patent Application Publication No. 2014-050406 (Paragraph 0102)

SUMMARY OF THE INVENTION

Problem to be Solved by the Invention

It is a usual practice to use a dedicated desulfurization device for removing hydrogen sulfide and a dedicated deoxidization device for removing oxygen. It is costly to be equipped with these two devices. Furthermore, when a copper catalyst is used as the deoxidization device, it is required to heat it at a high temperature.

In view of the above, it is an object of the present invention to remove or reduce concentration of the hydrogen sulfide and the oxygen in the gas by a simple structure, thereby downsizing the facility and reducing the cost.

Means for Solving the Problems

To solve the problems mentioned above, a method of the present invention provides a method for treating gas containing hydrogen sulfide and oxygen as target constituents of removal or reduction in concentration, the method comprising steps of:

measuring hydrogen sulfide content and oxygen content of the gas;

contacting a material containing transition metal and the gas after the measurements or before the measurements, the material containing transition metal becoming a product that is reactable with one of the hydrogen sulfide and the oxygen by reacting with the other of the hydrogen sulfide and the oxygen; and selecting whether to execute or omit or simplify an additional step for the removal or reduction in concentration of said one according to results of the measurements.

The transition metal constituting the material containing transition metal may be iron (Fe), manganese (Mn) or zinc (Zn), for example. Preferably, the transition metal is iron (Fe) or manganese (Mn).

The material containing transition metal may be transition metal oxide such as iron oxide, manganese oxide and zinc oxide or transition metal sulfide such as iron sulfide, manganese sulfide and zinc sulfide. Preferably, the material containing transition metal is iron oxide or manganese oxide, or iron sulfide or manganese sulfide.

For example, iron oxide reacts with hydrogen sulfide to become iron sulfide (Formulas 1 and 2).

$$Fe_2O_3 \cdot 3H_2O + 3H_2S \rightarrow Fe_2S_3 + 6H_2O \quad \text{(Formula 1)}$$

$$FeO + H_2S \rightarrow FeS + H_2O \quad \text{(Formula 2)}$$

The produced iron sulfide can react with oxygen ($O_2$). By this reaction, the iron sulfide returns to the iron oxide (Formulas 3 to 5).

$$Fe_2S_3 + 3/2 O_2 + nH_2O \rightarrow Fe_2O_3 \cdot nH_2O + 3S \rightarrow Fe_2O_3 + nH_2O + 3S \quad \text{(Formula 3)}$$

$$4FeS + 7O_2 \rightarrow 2Fe_2O_3 + 4SO_2 \quad \text{(Formula 4)}$$

$$2FeS + 3O_2 \rightarrow 2FeO + 2SO_2 \quad \text{(Formula 5)}$$

In a case where the reactant is iron sulfide, iron oxide is produced by reaction with oxygen (Formulas 3 to 5). The produced iron oxide returns to the iron sulfide by reaction with the hydrogen sulfide (Formulas 1 and 2).

This means that at least a part of the iron oxide (or the iron sulfide) acts catalytically in a reaction to remove hydrogen sulfide and oxygen. Therefore, depending on a composition ratio of the hydrogen sulfide and the oxygen in the gas, both of the hydrogen sulfide and the oxygen can be removed almost entirely or to some degree in the contacting step. In this case, the additional step can be omitted or simplified. Thus, facilities for the additional step can be downsized or omitted. Thereby, facility cost can be reduced.

Manganese oxide reacts with hydrogen sulfide to become manganese oxide. And the manganese sulfide reacts with oxygen ($O_2$) to become manganese oxide. Therefore, manganese acts catalytically in a reaction to remove hydrogen sulfide and oxygen in a similar manner to iron.

Zinc oxide reacts with hydrogen sulfide to become zinc sulfide. And the zinc sulfide reacts with oxygen ($O_2$) to become zinc sulfate ($ZnSO_4$). Zinc sulfate does not react with hydrogen sulfide. Therefore, it is not feasible to use zinc catalytically in a reaction to remove hydrogen sulfide and oxygen for a long period of time. However, zinc may be used in a one-way reaction from zinc oxide to zinc sulfide, then to zinc sulfate.

Preferably, transition metal oxide (iron oxide, manganese oxide, zinc oxide or the like) is contacted with the gas in the contacting step, the transition metal oxide becoming a product that is reactable with oxygen by reaction with the hydrogen sulfide, and selection is made whether to deoxidize the gas after the contacting or omit or simplify the deoxidization according to the results of the measurements.

When the oxygen content is less than the hydrogen-sulfide content, omission or simplification of the deoxidization may be selected and when the oxygen content is greater than the hydrogen-sulfide content, execution of the deoxidization may be selected (step of determining necessity of deoxidization).

Alternatively, the transition metal sulfide (iron sulfide, manganese sulfide, or the like) that can become a product reactable with the hydrogen sulfide by reaction with the oxygen may be contacted with the gas in the contacting step, and depending on the results of the measurements, selection may be made whether to remove hydrogen sulfide from the gas after the contacting step or omit or simplify the removal of the hydrogen sulfide.

Preferably, transition metal oxide (iron oxide, manganese oxide, zinc oxide or the like) is contacted with the gas in the contacting step, the transition metal oxide becoming a product that is reactable with oxygen by reaction with the hydrogen sulfide, and selection is made whether to add hydrogen sulfide or a sulfur compound other than the hydrogen sulfide to the gas before or during the contacting or omit the adding according to the results of the measurements or demand by a utilizing part of the gas (step of determining necessity of adding sulfur compound).

When the oxygen content is less than the hydrogen-sulfide content, omission of the adding may be selected. When the oxygen content is greater than the hydrogen-sulfide content, execution of the adding may be selected. By making the gas before or during the contacting step hydrogen sulfide-rich in this manner, not only the hydrogen sulfide but also the oxygen can be sufficiently removed or reduced in concentration.

Alternatively, the transition metal sulfide (iron sulfide, manganese sulfide, or the like) that can become a product reactable with the hydrogen sulfide by reaction with the oxygen may be contacted with the gas in the contacting step, and depending on the results of the measurements, selection may be made whether to add oxygen to the gas before or during the contacting step or omit the adding of the oxygen.

An example of the sulfur compound other than the hydrogen sulfide may be sodium sulfide ($Na_2S$).

The utilizing part of the gas may be a culture tank in which gas-utilizing microorganisms are cultured in liquid culture medium therein.

Preferably, the gas after the treatment is provided to liquid culture medium for culturing gas-utilizing microorganisms therein. The gas-utilizing microorganisms intake CO or the like in the gas and produce valuable materials by fermentation. The gas-utilizing microorganisms can be cultured in a stable manner by supplying the target gas to the liquid culture medium after removing or reducing in concentration of the oxygen or the like.

The hydrogen sulfide contains sulfur (S) that is an element necessary for the gas-utilizing microorganisms, and essentially there is no need to remove the hydrogen sulfide. However, when treating the gas to remove oxygen or acetylene using a noble metal catalyst or a base metal catalyst, sulfur (S) can be a typical poisoning substance to these catalysts. Therefore, it is necessary to reduce the hydrogen sulfide level to a ppm level or to a ppb level depending on the catalyst. The gas such as the syngas commonly contains hydrogen sulfide in a concentration of several-ten ppm. Therefore, if the concentration of the hydrogen sulfide is to be reduced to several ppm to ppb level, the cost therefor will be very high. Moreover, it may be required to supplement the sulfur (S) needed by the gas-utilizing microorganisms by adding sodium sulfide or the like in a separate step. This is an inefficient system to supplement the sulfur (S) once removed.

On the other hand, according to the method including the step of determining, necessity of deoxidization or the step of determining the necessity of adding sulfur compound, it is not required to use a catalyst for removing oxygen or the like. Therefore, there will be no problem even if some hydrogen sulfide remains in the gas. This will lighten the burden of removal facility. At the same time, adding may not be required or an amount to be added may be reduced in facilities for adding sulfur compound. Thereby, synergistic effects may be expected.

Advantageous Effects of the Invention

According to the present invention, the additional step for removing the other of the hydrogen sulfide and oxygen may not be required or facilities therefor can be downsized. Therefore, facilities can be downscaled and facility cost can be reduced.

MODE FOR CARRYING OUT THE INVENTION

Embodiments of the present invention will be described hereinafter with reference to the drawings.

First Embodiment

Figure 1:
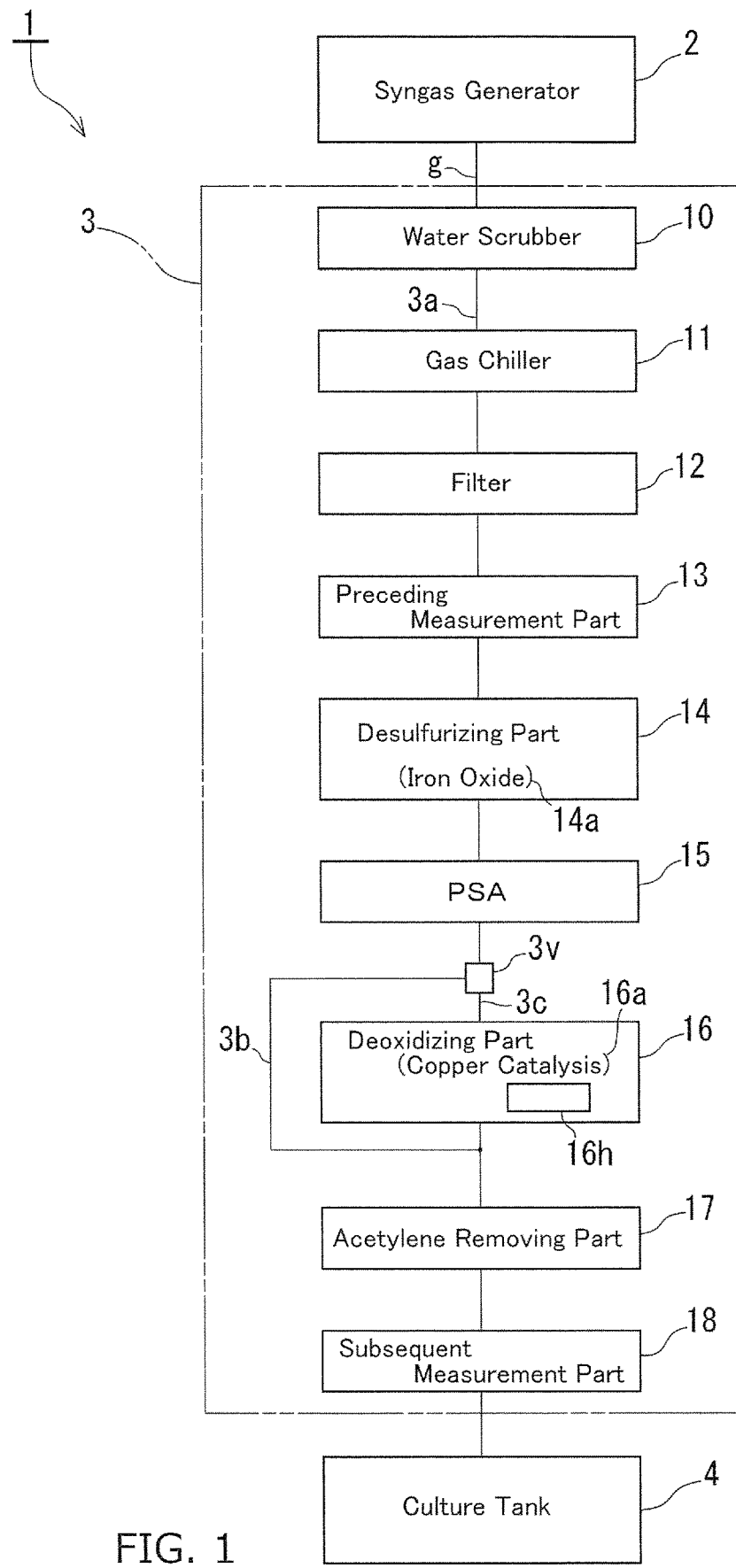
FIG. 1 is a block diagram schematically showing a valuable materials producing system according to a first embodiment of the present invention.

As shown in FIG. 1, a valuable materials producing system 1 includes a gas treatment part 3 and a culture tank 4. A syngas generator 2 is provided before the valuable materials producing system 1. The syngas generator 2 is a waste disposal facility in this embodiment. Wastes may include municipal wastes, tires, biomass, wooden chips and plastic wastes. The syngas generator 2 is provided with a melting furnace. In the melting furnace, the wastes are burnt by a highly-concentrated oxygen gas and decomposed to a low-molecular level. Eventually, syngas g (target gas) is generated.

The syngas g derived from wastes includes CO and $H_2$ as useful constituents. Moreover, the syngas g includes hydrogen sulfide ($H_2S$) and oxygen ($O_2$) as target substances of removal or reduction in concentration. The syngas g further includes $CO_2$, water content ($H_2O$), solid impure substance, naphthalene, benzene (BTEX) and acetylene ($C_2H_2$) or the like as target substances of removal or reduction in concentration.

The gas treatment part 3 includes a passage 3a for the syngas g. The gas passage 3a is provided with a water scrubber 10, a gas chiller 11, a filter 12, a preceding measurement part 13, a desulfurizing part 14, a PSA (pressure-swing adsorption) 15, a deoxidizing part 16, an acetylene removing part 17 and a subsequent measurement part 18 in this order from an upstream side.

Although not shown in detail in the drawings, the preceding measurement part 13 includes a concentration measuring portion and an integral processing portion. A concentration of the hydrogen sulfide and a concentration of oxygen in the syngas g are measured in the concentration measuring portion. Measured values of the hydrogen sulfide concentration and measured values of the oxygen concentration are respectively integrated over a certain measurement time in the integral processing portion. The time-integrated values respectively correspond to hydrogen sulfide content of the syngas g and oxygen content of the syngas g that passed through the preceding measurement part 13 over the measurement time.

The desulfurizing part 14 is provided with a desulfurizing agent 14a. A transition metal oxide (reactant containing transition metal) is used as the desulfurizing agent 14a. The transition metal may be iron (Fe), manganese (Mn) or zinc (Zn). Particularly, the transition metal is preferably iron or manganese.

In this embodiment, iron is used as the transition metal. The desulfurizing agent 14a includes iron oxide ($Fe_2O_3$, FeO). Thereby, material cost can be reduced and handling of the material can be eased.

PSA 15 is provided with zeolite, silica gel, activated carbon or the like as adsorbent.

The deoxidizing part 16 is provided with a deoxidizing agent 16a. A copper catalyst, for example, is used as the deoxidizing agent 16a. The deoxidizing part 16 is provided with a heater 16h. Heating temperature of the heater 16h may be set at around 150 to 400 degrees C., for example.

In place of the copper (Cu), platinum (Pt), nickel (Ni) or the like may be used as the metal catalyst as the deoxidizing agent 16a.

The gas passage 3a is provided with a shortcut passage 3b. The deoxidizing part 16 can be skipped by the shortcut passage 3b. A branch portion of the shortcut passage 3b is provided with a direction control valve 3v (selection means), which is a three-way valve.

The acetylene removing part 17 is provided with a noble metal such as palladium (Pd), platinum (Pt) or the like as an acetylene removal catalyst.

The subsequent measurement part 18 includes a concentration measuring portion and an integral processing portion in a similar manner to the preceding measurement part 13.

The culture tank 4 is connected subsequent to the gas treatment part 3. Liquid culture medium is stored in the culture tank 4. Anaerobic gas-utilizing microorganisms are cultured in the liquid culture medium. Anaerobic bacteria such as those disclosed in the Patent Document 1 given above, International Publication No. WO2011/087380, United States Patent Application Publication No. 2013/0065282 or the like may be used as the gas-utilizing microorganisms. Valuable materials such as ethanol ($C_2H_5OH$) are produced from the syngas g by metabolism of the gas-utilizing microorganisms.

Though not shown in the drawings, a refiner including a distillation tower is provided subsequent to the culture tank 4.

A method for producing ethanol (valuable material) using the valuable materials producing system 1 will be described hereinafter.

The syngas g is generated by burning wastes in the syngas generator 2 (Gas Generating step).

The syngas g is introduced to the gas treatment part 3. In the gas treatment part 3, the syngas g is purified by removing or reducing concentration of the target substance in the syngas g.

Specifically, water soluble impure substances in the syngas g are removed in the water scrubber 10 first.

Then, in the gas chiller 11, the water content ($H_2O$) and naphthalene or the like in the syngas g are removed. The water content may be left in a certain quantity for a deoxidizing step (Formula 3) or the like to be described later.

Then, solid impure substances in the syngas g are removed by the filter 12.

<Measuring Step>

A concentration of the hydrogen sulfide and a concentration of the oxygen in the syngas g are measured in the preceding measurement part 13. The hydrogen sulfide content and the oxygen content of the syngas g that passed through the preceding measurement part 13 over a certain measurement time are calculated by integrating the measured values over time.

<Contacting Step>

The syngas g is then introduced to the desulfurizing part 14 and contacted with the desulfurizing agent 14a including of iron oxide. Thereby, reactions as follows occurs (Hydrogen Sulfide Removing Step):

$$Fe_2O_3 \cdot 3H_2O + 3H_2S \rightarrow Fe_2S_3 + 6H_2O \quad \text{(Formula 1)}$$

$$FeO + H_2S \rightarrow FeS + H_2O \quad \text{(Formula 2)}$$

As a result, the hydrogen sulfide (one of the gas constituents) can be removed (or reduced in concentration). Moreover, iron sulfide is produced as a reaction product.

The produced iron sulfide can react with oxygen ($O_2$) as shown in the following formulas. Thereby, the oxygen (the other gas constituent) in the syngas g can also be removed (or reduced in concentration) (Deoxidizing Step).

$$Fe_2S_3 + 3/2 O_2 + nH_2O \rightarrow Fe_2O_3 \cdot nH_2O + 3S \rightarrow Fe_2O_3 + nH_2O + 3S \quad \text{(Formula 3)}$$

$$4FeS + 7O_2 \rightarrow 2Fe_2O_3 + 4SO_2 \quad \text{(Formula 4)}$$

$$2FeS + 3O_2 \rightarrow 2FeO + 2SO_2 \quad \text{(Formula 5)}$$

Moreover, the iron sulfide returns to iron oxide by reaction with oxygen. That is, at least a part of the iron oxide acts catalytically in a reaction to remove hydrogen sulfide and oxygen. Therefore, when the oxygen content of the syngas g is less than the hydrogen sulfide content thereof to a certain degree, not only the hydrogen sulfide but also the oxygen can be sufficiently removed in the desulfurizing part 14.

Then the benzene (BTEX) and the $CO_2$ or the like in the syngas g are removed by adsorption in the PSA 15.

<Selecting Step>

Then, according to the results of the measurements in the preceding measurement part 13, selection is made whether to execute or omit or simplify an additional step for removing oxygen from the syngas g. That is, selection is made whether to further deoxidize the syngas g after the contacting step or omit or simplify the deoxidization (Determining Necessity of Deoxidization).

Specifically, when the oxygen content is greater than the hydrogen sulfide content in the preceding measurement part 13, execution of deoxidization is selected. That is, the shortcut passage 3b is shut off and the passage 3c to the deoxidizing part 16 is opened by the direction control valve 3v. Thereby, the syngas g is introduced to the deoxidizing part 16. Residual oxygen in the syngas g reacts with the deoxidizing agent 16a including copper (Cu) in the deoxidizing part 16. Thereby, the residual oxygen can be removed (or reduced in concentration) (Step of Additional Deoxidization). At this time, the deoxidizing agent 16a is heated to around 150 to 400 degrees C., for example with the heater 16h. Thereby, the deoxidization can be facilitated.

On the other hand, when the oxygen content is less than the hydrogen sulfide content by certain value in the preceding measurement part 13, the shortcut passage 3b is opened and the passage 3c to the deoxidizing part 16 is shut off by the direction control valve 3v. Thereby, the syngas g is made to pass through the shortcut passage 3b. Therefore, the step of additional deoxidization in the deoxidizing part 16 is omitted.

Since the oxygen is sufficiently removed in the desulfurizing part 14 when the oxygen content is less than the hydrogen sulfide content by certain value, it is not required to additionally deoxidize in the deoxidizing part 16.

If the oxygen content is close to the hydrogen sulfide content even when the oxygen content is less than the hydrogen sulfide content, the step of additional deoxidization may be executed in the deoxidizing part 16 for insurance.

Next, acetylene in the syngas g is removed in the acetylene removing part 17.

Then, composition of the syngas g is measured in the subsequent measurement part 18. Particularly, residual volumes of the hydrogen sulfide and the oxygen in the syngas g are measured.

When the hydrogen sulfide and oxygen remain, it is preferable to treat the syngas to remove them with a hydrogen sulfide remover (PSA) and an oxygen remover (copper catalysis) or the like in a separate step. Since the remaining amount should be small even in this case, the load of the separate step for removing treatment should be light, and the device configuration can be simplified.

The necessity of deoxidization may be determined according to the results of the measurements in the subsequent measurement part 18 in place of determining the necessity of deoxidization according to the results of the measurements in the preceding measurement part 13. That is, when the oxygen content measured by the subsequent measurement part 18 is greater than a predetermined amount, the execution of the step of additional deoxidization may be selected by introducing the syngas g to the deoxidizing part 16. When the oxygen content measured by the subsequent measurement part 18 is less than the predetermined amount, the step of additional deoxidization may be omitted by making the syngas g pass though the shortcut passage 3b.

After that, the syngas g is supplied to the liquid culture medium in the culture tank 4. Thereby, the gas-utilizing microorganisms in the culture medium intake CO and $H_2$ or the like in the syngas g and produce the valuable materials such as ethanol by fermentation (Step of Producing Valuable Materials).

By removing impure substances such as oxygen in the syngas g beforehand, the gas-utilizing microorganisms can be cultured in a stable manner.

A portion of the liquid culture medium in the culture tank 4 is introduced to the distillation tower (not shown) and distilled (Refining Step). Thereby, valuable materials such as ethanol can be extracted.

Since the desulfurizing part 14 also serves as the deoxidizing part in the valuable materials producing system 1, the dedicated deoxidizing part 16 can be downsized or simplified and a required amount of the deoxidizing agent 16a can be reduced or frequency of use of the deoxidizing agent 16a can be constrained. Moreover, a required heating capacity of the heater 16h can be reduced. Since the deoxidization by iron sulfide in the desulfurizing part 14 does not require heating, it is not required to provide the desulfurizing part 14 with a heater. Therefore, the facility cost can be constrained.

Moreover, since the desulfurizing agent 14a can be reproduced at the same time with being consumed, a life of the desulfurizing agent 14a can be extended.

Other embodiments of the present invention will be described hereinafter. Same reference numerals are used in the drawings to designate parts that correspond to those in the foregoing embodiment and description thereof will be omitted as appropriate.

Second Embodiment

Figure 2:
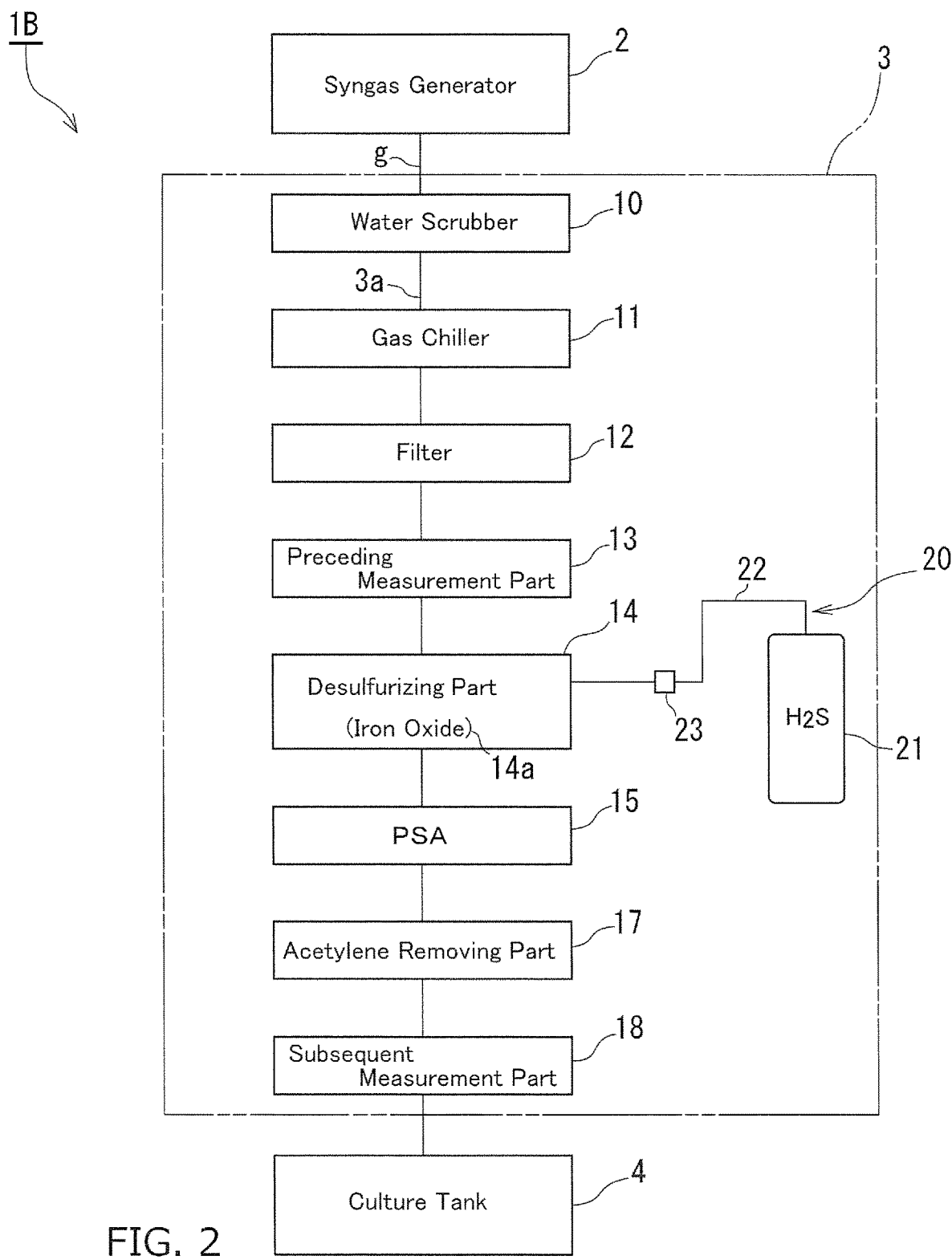
FIG. 2 is a block diagram schematically showing a valuable materials producing system according to a second embodiment of the present invention.

As shown in FIG. 2, a valuable materials producing system 1B according to a second embodiment includes a hydrogen sulfide adding part 20. The hydrogen sulfide adding part 20 includes a hydrogen sulfide supply source 21, an addition passage 22 and an on-off valve 23. Hydrogen sulfide is stored in the hydrogen sulfide supply source 21. The addition passage 22 extends from the hydrogen sulfide supply source 21. The addition passage 22 is provided with the on-off valve 23. A downstream end of the addition passage 22 is connected to a desulfurizing part 14.

A deoxidizing part 16 is omitted in the valuable materials producing system 1B. The valuable materials producing system 1B is not provided with a shortcut passage 3b and a direction control valve 3v either.

In the second embodiment, selection is made whether to execute or omit addition of hydrogen sulfide to the syngas g as an additional step for removing oxygen from the syngas g according to results of measurements of hydrogen sulfide content and oxygen content in a preceding measurement part 13 (Selecting Step).

Specifically, when molar content of oxygen is greater than molar content of hydrogen sulfide in the preceding measurement part 13, the addition is executed. That is, by opening the on-off valve 23, the hydrogen sulfide from the hydrogen sulfide supply source 21 is added to the desulfurizing part 14 via the addition passage 22. The amount to be added may be determined based on a difference between the oxygen content and the hydrogen sulfide content in the preceding measurement part 13, for example. Thereby, the syngas g in the desulfurizing part 14 can be constantly hydrogen sulfide-rich (oxygen content<hydrogen sulfide content). Thus, the hydrogen sulfide in the syngas g can be removed by the hydrogen sulfide removing reaction of the desulfurizing agent 14a (iron oxide), and furthermore, the oxygen in the syngas g can be sufficiently removed by the iron sulfide in the product of the reaction.

On the other hand, when the molar content of oxygen is less than the molar content of hydrogen sulfide by certain value in the preceding measurement part 13, the addition is omitted. That is, the on-off valve 23 is closed. Therefore, the hydrogen sulfide in the hydrogen sulfide supply source 21 is not added to the desulfurizing part 14. Without adding the hydrogen sulfide, the oxygen in the syngas g can be sufficiently removed by the iron sulfide in the product of the reaction to remove the hydrogen sulfide.

Accordingly, regardless of whether the execution of addition or omission of addition is selected, it is hardly necessary to remove oxygen by a dedicated deoxidizing part 16 (see FIG. 1) afterwards. Therefore, the deoxidizing part 16 can be omitted or simplified. Even when the deoxidizing part 16 is provided, a small deoxidizing part 16 is enough.

The present invention is not limited to the embodiments described above. Various modifications can be made without departing from the scope and spirit of the invention.

For example, in place of the iron oxide, manganese oxide, zinc oxide or a mixture thereof may be used as the desulfurizing agent 14a in the desulfurizing part 14.

The valuable materials producing system 1 may be provided with a deoxidizing part including iron sulfide or manganese sulfide in place of the desulfurizing part 14. A dedicated desulfurizing part may be provided in place of the deoxidizing part 16. When the oxygen content is greater than the hydrogen sulfide content by certain value, the dedicated desulfurizing part may be omitted or simplified. When the oxygen content is less than the hydrogen sulfide content, the execution of desulfurization by a dedicated desulfurizing part may be selected.

The valuable materials producing system 1B may be provided with a deoxidizing part including iron sulfide or manganese sulfide in place of the desulfurizing part 14. An oxygen supply source may be provided in place of the hydrogen sulfide supply source 21. When the oxygen content of the syngas g is less than the hydrogen sulfide content of the syngas g, oxygen may be added to the syngas g from the oxygen supply source to make the syngas g oxygen rich (oxygen content>hydrogen sulfide content).

In the valuable materials producing system 1B, the addition passage 22 may be joined a gas passage 3a between the preceding measurement part 13 and the desulfurizing part 14. The hydrogen sulfide form the hydrogen sulfide supply source 21 may be added to the gas passage 3a between the preceding measurement part 13 and the desulfurizing part 14.

The target valuable material to be produced in the culture tank 4 is not limited to ethanol. Alternatively, the target valuable material may be acetic acid or methanol or the like.

The syngas g may be by-product gas of a steel plant (gas from a converter, a blast furnace or the like).

The gas generator 2 is not limited to the waste disposal facility. Alternatively, the gas generator 2 may be a steel plant, a coal power plant or the like.

INDUSTRIAL APPLICABILITY

The present invention may be applied to an ethanol producing system, for example, in which ethanol is produced from syngas generated in an incineration disposal of industrial wastes.

EXPLANATION OF REFERENCE NUMERALS

1, 1B valuable materials producing system
2 syngas generator
3 gas treatment part
3a gas passage
3b shortcut passage
3c passage to the deoxidizing part 16
3v direction control valve
4 culture tank (utilizing part)
10 water scrubber
11 gas chiller
12 filter
13 preceding measurement part
14 desulfurizing part
14a desulfurizing agent
15 PSA
16 deoxidizing part
16a deoxidizing agent
16h heater
17 acetylene removing part
18 subsequent measurement part
20 hydrogen sulfide adding part
21 hydrogen sulfide supply source
22 addition passage
23 on-off valve
g syngas (target gas)

The invention claimed is:

1. A method for treating a gas containing hydrogen sulfide and oxygen as target constituents of removal and/or reduction in concentration, the method comprising steps of:
    a measuring step of measuring hydrogen sulfide content and oxygen content of the gas;
    a contacting step of contacting a material containing a transition metal and the gas after the measuring step,
        wherein the material becomes a product containing the transition metal by reacting the material with one of the hydrogen sulfide and the oxygen in the gas,
        wherein the product reacts with the other of the hydrogen sulfide and the oxygen in the gas;
    a selecting step of selecting whether to perform a deoxidation step of bringing the gas into contact with a deoxidizing metallic catalyst,
        wherein, when the oxygen content is greater than the hydrogen sulfide content in the measuring step, the deoxidation step is performed after the contacting step, and
        wherein, when the oxygen content is less than the hydrogen sulfide content in the measuring step, the gas is bypassed away from the deoxidizing metallic catalyst by passing through a shortcut passage; and
    a performing step of either performing the deoxidation step or bypassing the gas away from the deoxidizing metallic catalyst according to the selecting step,
    wherein the selecting step is performed according to the result of the measuring step before the contacting step.

2. The method for treating gas according to claim 1,
    wherein the transition metal comprises at least one selected from the group consisting of iron, manganese, and zinc.

3. The method for treating gas according to claim 1, further comprising, after the performing step, a step of providing the gas to a liquid culture medium for culturing gas-utilizing microorganisms therein.

* * * * *